US012558084B2

(12) United States Patent (10) Patent No.: US 12,558,084 B2
Halverson et al. (45) Date of Patent: Feb. 24, 2026

(54) SYSTEMS AND METHODS FOR MEASURING AND APPLYING A SPINAL COMPRESSION FORCE

(71) Applicant: Nexus Spine, LLC, Salt Lake City, UT (US)

(72) Inventors: Peter A Halverson, Draper, UT (US); David T. Hawkes, Pleasant Grove, UT (US)

(73) Assignee: NEXUS SPINE, LLC, Salt Lake City, UT (US)

( * ) Notice: Subject to any disclaimer, the term of this patent is extended or adjusted under 35 U.S.C. 154(b) by 119 days.

(21) Appl. No.: 18/238,216

(22) Filed: Aug. 25, 2023

(65) Prior Publication Data

US 2024/0065684 A1 Feb. 29, 2024

Related U.S. Application Data

(60) Provisional application No. 63/401,104, filed on Aug. 25, 2022.

(51) Int. Cl.
| | |
|---|---|
| *A61B 17/02* | (2006.01) |
| *A61F 2/46* | (2006.01) |
| *A61B 17/56* | (2006.01) |
| *A61B 17/68* | (2006.01) |

(52) U.S. Cl.
CPC .......... *A61B 17/025* (2013.01); *A61F 2/4611* (2013.01); *A61B 2017/0256* (2013.01); *A61B 2017/564* (2013.01); *A61B 2017/681* (2013.01); *A61F 2002/4628* (2013.01); *A61F 2002/4666* (2013.01)

(58) Field of Classification Search
CPC ......... A61B 17/02; A61B 17/025; A61F 2/46; A61F 2/4611; A61F 2/4657; A61F 2/4684
See application file for complete search history.

(56) References Cited

U.S. PATENT DOCUMENTS

| | | | | |
|---|---|---|---|---|
| 4,066,082 | A * | 1/1978 | Arcan .................... | A61B 5/224 |
| | | | | 73/818 |
| 2003/0055430 | A1 | 3/2003 | Kim | |
| 2004/0059261 | A1* | 3/2004 | Grinberg ................ | A61B 90/06 |
| | | | | 600/587 |
| 2004/0236342 | A1 | 11/2004 | Ferree et al. | |
| 2010/0082029 | A1 | 4/2010 | Ibrahim et al. | |
| 2011/0257655 | A1 | 10/2011 | Copf | |
| 2011/0319755 | A1 | 12/2011 | Stein et al. | |
| 2018/0125598 | A1* | 5/2018 | McAfee ............. | A61B 17/7077 |

OTHER PUBLICATIONS

International Search Report and Written Opinion issued by the International Search Authority for related Int. PCT Application No. PCT/US/23/31174, dated Jan. 29, 2024.

* cited by examiner

*Primary Examiner* — Christopher J Beccia
(74) *Attorney, Agent, or Firm* — Bryant J. Keller; John Oldroyd; Kirton McConkie

(57) ABSTRACT

Systems and methods for measuring and applying a spinal compression force are provided. Some implementations of the systems and methods include a compression instrument having one or more compressors or gauges. In some cases, the compressor is configured to apply the spinal compression force to a spine of a patient. In some cases, the gauge is configured to measure the spinal compression force. Other implementations are discussed herein.

19 Claims, 7 Drawing Sheets

100

100

100

100

100

SYSTEMS AND METHODS FOR MEASURING AND APPLYING A SPINAL COMPRESSION FORCE

CROSS-REFERENCE TO RELATED APPLICATION

This application claims priority to U.S. Provisional Patent Application Ser. No. 63/401,104, filed Aug. 25, 2022, and entitled "METHODS AND INSTRUMENTS FOR APPLYING COMPRESSION TO THE SPINE"; which is incorporated herein by reference in its entirety.

FIELD

The present disclosure relates to spinal compression, and more particularly to systems and methods for measuring and applying a spinal compression force.

BACKGROUND AND RELATED ART

Treatment of spinal conditions often requires spinal surgery, such as spinal fusion surgery. During some spinal procedures, the spine may be distracted or compressed to allow implantation of interbody devices or to surgically alter the soft or hard tissues surrounding the spine. In some such instances, it is often desirable to apply compression (or extension) to the spine. For example, proper application of compression or extension may help facilitate bone growth, correct deformities (e.g., deformities caused by trauma, deformities caused by scoliosis, and other deformities), and lead to a proper sagittal balance through correction of lordosis (inward curve of the lumbar spine) or kyphosis (exaggerated forward rounding of the upper back).

In many cases, one or more spinal implants are affixed to or inserted between a patient's spinal vertebrae to apply the desired degree of compression. However, determining the proper size of implant to use (or the optimal distance to separate spinal vertebrae from one another) can be difficult for several reasons. For example, the proper space between vertebrae may differ based on many factors, such as: the location of the vertebrae within the spine (e.g., the spinal segments in which the vertebrae are located); the stiffness of the vertebrae; the amount of muscle, fat, and other tissue surrounding the vertebrae (especially where tissue has been removed as part of the operation in question); the size of the spinal vertebrae; and the individual anatomy of the patient in question. Accordingly, vertebrae separation (e.g., the implant size) is often determined subjectively. In some cases, a physician applies a subjective amount of force to spinal vertebrae in order to "get a feel for" the proper size of implant to use. In some cases, a physician hammers (or otherwise inserts "trials" representing various sized implants between the vertebrae, then subjectively determines which size of implant to use based on the physician's opinion about which trial fit best.

During the process of determining the correct spinal implant configuration, many forces are often applied to the spine of the patient. For example, a physician may squeeze (or otherwise actuate) a tool to apply a force. Vibration and sharp forces may also be applied when a physician is hammering trials into the patient's spine. These forces can cause damage to the spine, surrounding tissue, or other parts of the patient's body, thereby causing pain, disfunction, or other problems (which may be significant and long lasting, or even permanent).

Moreover, using an improper implant configuration (e.g., selecting a size of implant that places too much or too little pressure on vertebrae) can lead to bone fracture, bone resorption, lack of bone growth, and other severe problems. Thus, spinal operations can, in some cases, cause more problems than they solve.

Thus, while there are known techniques for treating spinal conditions, such techniques are not necessarily without their shortcomings, particularly (as described above) with relation to spinal fusion surgery, spinal compression, and selection of proper spinal implant configurations. Accordingly, it would be an improvement in the art to augment or even replace current techniques with other techniques.

BRIEF SUMMARY

Systems and methods for measuring and applying a spinal compression force are provided. Some implementations of the systems and methods include a compression instrument having one or more compressors or gauges. In some cases, the compressor is configured to apply the spinal compression force to a spine of a patient. In some cases, the gauge is configured to measure the spinal compression force.

In some implementations of the compression instrument, the compressor includes one or more arms, such as a first arm and a second arm (and any number of additional arms). In some cases, the first arm includes a first tip and a first handle. In some cases, the second arm includes a second tip and a second handle. Accordingly, some implementations of the compression instrument generally resemble a pair of calipers, scissors, pliers, reverse pliers, forceps, shears, clippers, grippers, or any other suitable two-armed tool. In some instances, applying a force to at least one of the first handle and the second handle causes at least one of the first tip and the second tip to move apart to apply the spinal compression force to the spine.

In some implementations, at least one of the first tip and the second tip is configured to selectively couple to one or more spinal implants. For example, in some implementations, the tip (e.g., either or both) is shaped and sized to correspond to an anchor (e.g., a screw, nail, bolt, rivet, shaft, or any other component configured to be attached to a patient's spine). In some implementations, one or more of the tips are configured to contact, couple directly to, or otherwise interface with the spine itself (e.g., by having a surface sized and shaped appropriately to contact a surface of a vertebra).

Some implementations of the instrument having multiple arms include one or more pivots or pivot joints. In some cases, the first arm and the second arm are movably coupled together to form the pivot. Some implementations include a pivot coupler (e.g., a screw, bolt, nail, rod, thread, hinge, articulation, axis, joint, bearing, or any other suitable type of fastener that could be used to couple multiple objects together to form a fulcrum, pivot, hinge, axle, spindle, or other static or dynamic connection point). In some implementations, the first arm is coupled to the second arm (e.g., via the pivot) such that when the first arm is biased toward the second arm (e.g., when a user squeezes the handles toward each other), the first tip is biased toward the second tip (e.g., the tips come together, as with traditional scissors). Some implementations of the first arm are coupled to the second arm (e.g., via the pivot) such that when the first arm is biased toward the second arm, the first tip is biased away from the second tip (e.g., the tips diverge, as with reverse pliers).

While the gauge can include any suitable component for measuring or conveying the compression force applied by the compression instrument, some implementations of the gauge include one or more indicators. In some cases, the indicator is configured to convey a measurement of the spinal compression force to a user. While the indicator may include any component suitable for conveying such a measurement, some implementations of the indicator include one or more needles, rods, shafts, arrows, sliders, dials, lasers, or other components configured to dynamically shift (e.g., change position, orientation, size, color, or any other perceivable characteristics) to display, emit, or otherwise convey one or more measurement values.

In some implementations, the compressor of the compression instrument includes (instead of or in addition to any of the features mentioned above or elsewhere herein) one or more housings. While the housing can include any component configured to form a particular shape or to house one or more other components, some embodiments of the housing are sized, shaped, and otherwise configured to be inserted into a spine. In some cases, the housing is configured to be inserted into a space between two vertebrae of the spine of the patient. Indeed, some iterations of the housing are configured to generally resemble a spinal implant trial. Some implementations include a trial arm (or guide), which, in some cases, is coupled or couplable to the housing.

In some implementations, the gauge includes one or more compression discs, which in some cases are optionally disposed within the housing. Although some implementations have only a single compression disc, some implementations include multiple compression discs. In some cases, the compression discs form a stack of discs.

In some implementations, one or more compression discs include one or more curved surfaces. In some cases, one or more of the curved surfaces are configured to flatten or become flatter when compressed. To illustrate, some implementations of the compression discs generally resemble a plate (or a disc, a ring, a sheet, leaf, or another substantially planar component) that is bent, bowed, or flexed, or that curves, ripples, undulates, or otherwise forms a shape that changes configuration when compressed. Thus, when the compression discs are compressed, the change in height of the compression discs (including a change in any particular compression disc on its own, or a change in a stack or collection of compression discs in the conglomerate) can be measured to determine a force applied to the gauge. In some cases, the compression discs are pre-calibrated to determine a precise force that correlates with a particular amount of change or deformation.

In some implementations having multiple compression discs, a first compression disc and a second compression disc are situated (e.g., within the housing) so that the curved surface of the first compression disc faces a first direction and the curved surface of the second compression disc faces a second direction. For example, in some embodiments, the first disc faces with the concave curved surface pointed in a downward or posterior direction (e.g., away from a lid of the housing) while the second disc faces with the concave curved surface pointed in an upward or anterior direction (e.g., toward the lid of the housing). In this manner, one or more gaps between the two discs (in a resting configuration) can be maximized (or otherwise configured) so that a change in height of the stack, when compressed, is more pronounced. In some instances, multiple compression discs are directly adjacent to each other, or even in contact with one another, whereas in some instances, multiple compression discs are present within the housing (or without) but are separated from each other by one or more barriers or another component.

In some implementations, the housing includes one or more lids or other openings. Indeed, in some cases, the housing includes a lid, which in some cases, is removable or openable. In some cases, the compression discs are interchangeable, allowing for discs with different stiffnesses, curvatures, thicknesses, or other characteristics to be placed within the housing. In some instances, this configuration allows for different numbers of discs to be placed within the housing. Accordingly, in some cases, a single instrument is useful for measuring multiple different ranges of compression forces.

In some implementations, the housing includes a pliable, flexible, or resilient material. Indeed, in some embodiments, the housing includes a pliable or flexible material that allows for the housing to be freely compressed. Thus, in some iterations, the compression discs provide substantially greater resistance to compression than the housing.

Some implementations of the compression instrument include a flexible or resilient element, such as a compression disc, an arm, or any other suitable flexible or resilient component. In some cases, the flexible or resilient element is configured to deflect when a spinal compression force is applied to the spine of the patient (e.g., in some cases, a compression disc is configured to flatten or become flatter, a rod is configured to bend, or another component is configured to otherwise deform, deflect, or change to another configuration). In some implementations, the gauge is configured to measure the applied spinal compression force based on the deflection of the flexible or resilient element. In some cases, the flexible or resilient member is flexible but not resilient, such that when the member is deformed, it maintains its shape to allow for a compression force to be easily measured, even after the compression instrument has been removed from the patient. In some cases, however, the flexible or resilient member is both flexible and resilient such that the compression instrument can be reused one or more times (e.g., many times following autoclaving).

To illustrate the foregoing, in some implementations, the flexible or resilient element includes a resilient arm that is configured to deflect when the spinal compression force is applied, and the gauge includes an indicator configured to measure the deflection of the arm. In some cases, the arm includes a first or a second arm of a compressor. In some cases, the indicator includes one or more needles (or one or more rods, shafts, bars, arrows, projections, dials, or any other suitable physical component capable of indicating a measurement based on its position). The needle, in some implementations, is coupled to the arm (in some cases, at or near the tip of the arm). In some implementations, the needle is coupled to the arm at a single location, so that when the arm is deflected or flexed, the needle remains in an unflexed configuration.

In some instances, the instrument includes one or more indicia. Although the indicia can include any indications of any kind that may aid in deciphering a measured value, in some cases, the indicia includes a scale having one or more markings that correspond to certain amounts of force applied to the arm. For example, in some cases in which a specific amount of force (e.g., 5 newtons, 150 newtons, or any other specified amount of force) is applied to the arm, the arm is deflected a certain distance, but the needle remains undeflected. Thus, in some cases, the distance between the initial position of the arm and its deflected position can be precisely determined through reference to the position of the needle relative to the arm. In some cases, the indicia can greatly aid a human being in making this determination (e.g., by including one or more markings that the needle points at when the arm is deflected with 1, 5, 10, 20, 50, 100, 150, 200, or 250 newtons of force, or any subrange of the foregoing).

In some implementations, the instrument includes one or more indicia where the flexible or resilient component includes the compression disc. For example, in some cases, the indicator is configured to measure a change in height of the stack of compression discs. Some iterations of the indicator include one or more indicia that correspond to a height of the stack at different compression loads.

In some implementations, the gauge includes or is otherwise configured to function with an air pressure sensor or any other suitable component for measuring a spinal compression force applied to the instrument. In some implementations, when a desired spinal compression force is applied using the instrument (as determined by the gauge), a spinal implant of the proper size (e.g., the size that would apply the desired amount of compression force) is inserted into the space between two vertebrae of the spine where the compression force was measured.

Some implementations of the systems and methods disclosed herein include a method for applying and measuring a spinal compression force. In some cases, the method (which can be varied in any suitable manner) includes one or more of the following: obtaining one or more compression instruments for applying one or more spinal compression forces; obtaining one or more gauges for measuring the spinal compression force; applying the spinal compression force with the instrument; and measuring the spinal compression force with the gauge.

In some implementations, the applying the spinal compression force with the instrument includes gradually increasing an application of the spinal compression force until the spinal compression force reaches a desired value, as measured with the gauge.

In some implementations, the desired value is anywhere between 1 newton and 350 newtons (or any subrange thereof). For example, in some implementations, the desired value is approximately between 50 newtons and 250 newtons, and in some implementations the desired value is between 75 newtons and 150 newtons.

In some implementations, the method includes measuring a distance between two spinal vertebrae when the spinal compression force reaches the desired value. In some cases, the measuring a distance is done with a tool separate from the one used to apply the compression, but, in some cases, the same tool is used for applying the compression and measuring the distance (and, in some cases, measuring the compression force as well). In some cases, the method includes inserting an implant having a thickness approximately equal to the distance as measured.

Some implementations of the disclosed systems and methods include a system for applying a desired amount of compression force to a patient's spine. In some instances, the system includes an instrument configured to apply a trial force to a pair of vertebrae of the patient's spine. While the instrument may be any suitable instrument (as discussed herein), in some implementations, the instrument includes one or more of a flexible or resilient element configured to deflect upon application of the trial force and a gauge for measuring the trial force based on a degree of deflection of the flexible or resilient element. In some implementations, the system includes a spinal implant configured to apply the desired amount of compression force to the patient's spine, in accordance with the trial force as measured. In some cases, the system includes a plurality of spinal implants having differing characteristics (e.g., different thicknesses, different materials, different stiffnesses, etc.), thereby allowing a healthcare worker to select a suitable spinal implant having the desired characteristics based on an applied compression force determined to be suitable through measurement of the force.

The systems and methods disclosed herein may be combined with one another in any suitable manner, and any element or portion of any disclosed system or method may be combined with any other element or portion of any disclosed system or method, unless expressly stated otherwise herein. Additional embodiments are discussed herein, and additional uses and features will be apparent to those of skill in the art based on this disclosure.

BRIEF DESCRIPTION OF THE DRAWINGS

The objects and features of the present disclosure will become more fully apparent from the following description and appended claims, taken in conjunction with the accompanying drawings. Understanding that these drawings depict only typical embodiments of the disclosed systems and methods and are, therefore, not to be considered limiting of its scope, the systems and methods will be described and explained with additional specificity and detail through the use of the accompanying drawings in which:

DETAILED DESCRIPTION

Systems and methods for measuring and applying a spinal compression force are provided. Some implementations of the systems and methods include a compression instrument having one or more compressors or gauges. In some cases, the compressor is configured to apply the spinal compression force to a spine of a patient. In some cases, the gauge is configured to measure the spinal compression force.

A description of embodiments will now be given with reference to the Figures. It is expected that the present systems and methods may take many other forms and shapes, hence the following disclosure is intended to be illustrative and not limiting, and the scope of the disclosure should be determined by reference to the appended claims.

Some embodiments of the disclosed systems and methods include one or more compressors configured to apply a spinal compression force. The term "compression" as used herein may refer to spinal compression, spinal extension, spinal distraction, and other forces operating on the spine, either as a whole or on one or more individual vertebrae (or other parts of the spine).

Although the compressor can include any component configured to apply a spinal compression force, various embodiments of compressors are disclosed herein. Likewise, some embodiments of the disclosed systems and methods include one or more gauges. Although the gauge may include any component configured to measure a spinal compression force, various embodiments of gauges are disclosed herein. In some embodiments, the compressor includes one or more flexible or resilient elements configured to deflect when the spinal compression force is applied. In some embodiments, the gauge measures the spinal compression force based on a deflection of the flexible or resilient elements. Accordingly, in some embodiments, the measurement of the spinal compression force can be correlated to a separation distance of two or more vertebrae of the spine, thus allowing for a spinal implant of a suitable size (and configured to apply the desired amount of compression) to be selected and inserted into the patient's spine. As a wide variety of systems and methods may be used to accomplish these purposes, various embodiments are disclosed below.

As shown in FIGS. 1-5C, some embodiments of the disclosed systems and methods include a compressor 100. As shown in FIGS. 1-4B, some embodiments of the compressor include one or more arms, such as a first arm 110 and a second arm 120 (and any number of additional arms). Although the arms may be any size and shape, and may include any suitable component that is useful for medical procedures or that can otherwise be associated with medical instruments, some embodiments of the compression instrument generally resemble a pair of calipers, scissors, pliers, reverse pliers, forceps, shears, clippers, grippers, or any other two-armed tool. Notwithstanding the foregoing, some embodiments have more than two arms, only one arm, or no arms at all.

Figure 1:
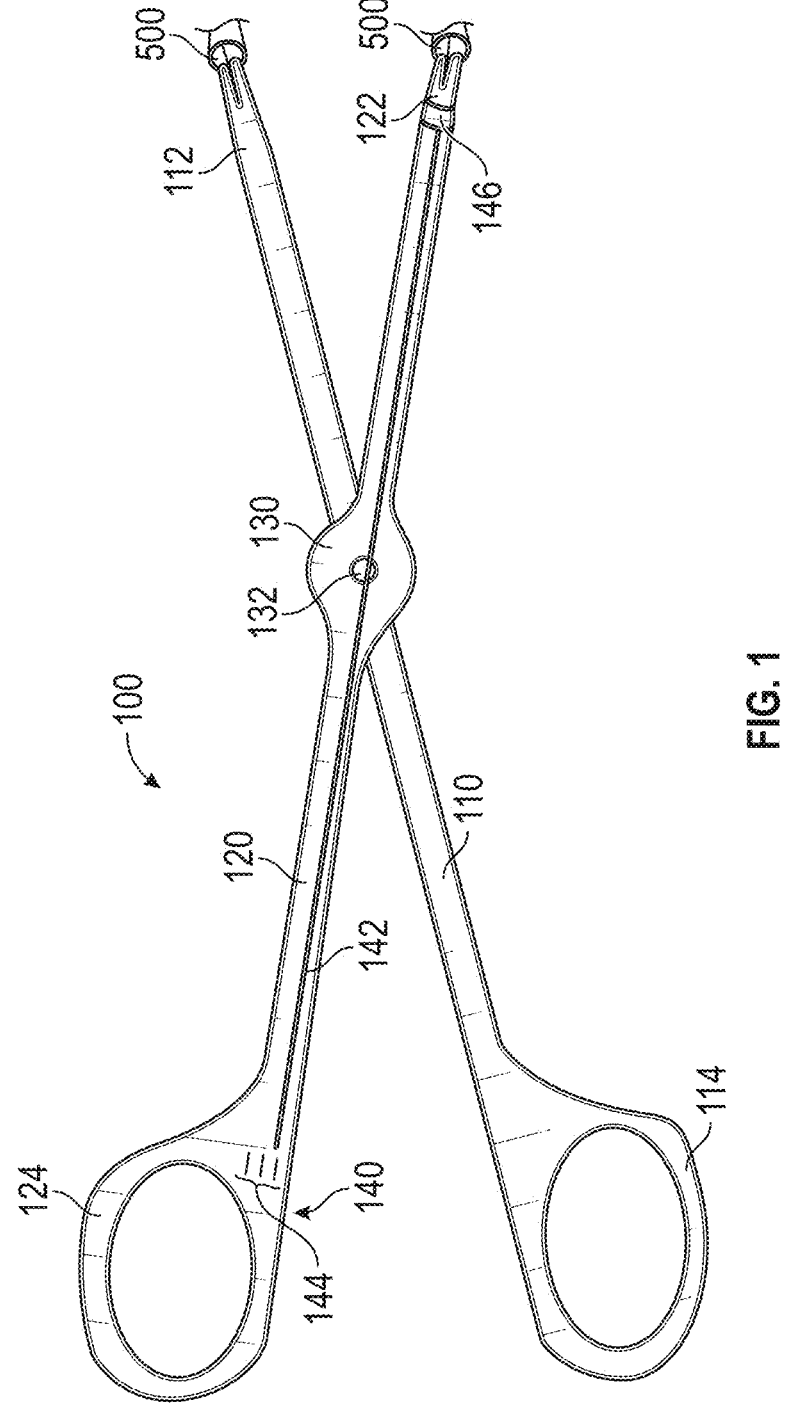
FIG. 1 shows a plan view of an instrument for measuring and applying a spinal compression force, in accordance with a representative embodiment.
Figure 2A:
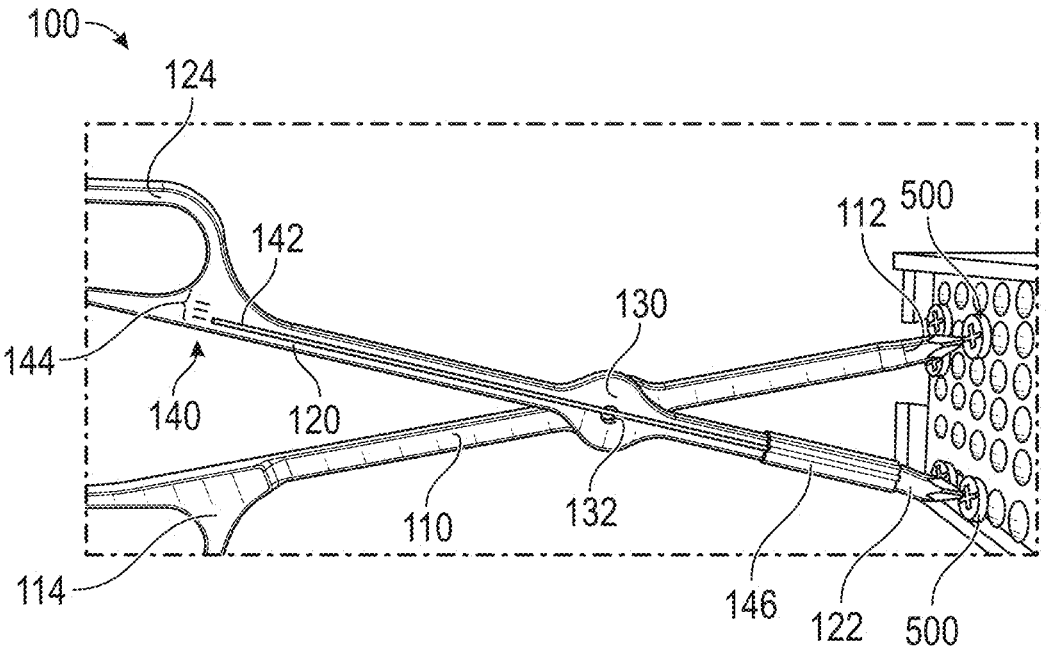
FIGS. 2A-2B show plan views of various configurations of the instrument for measuring and applying spinal compression force, in accordance with a representative embodiment.
Figure 2B:
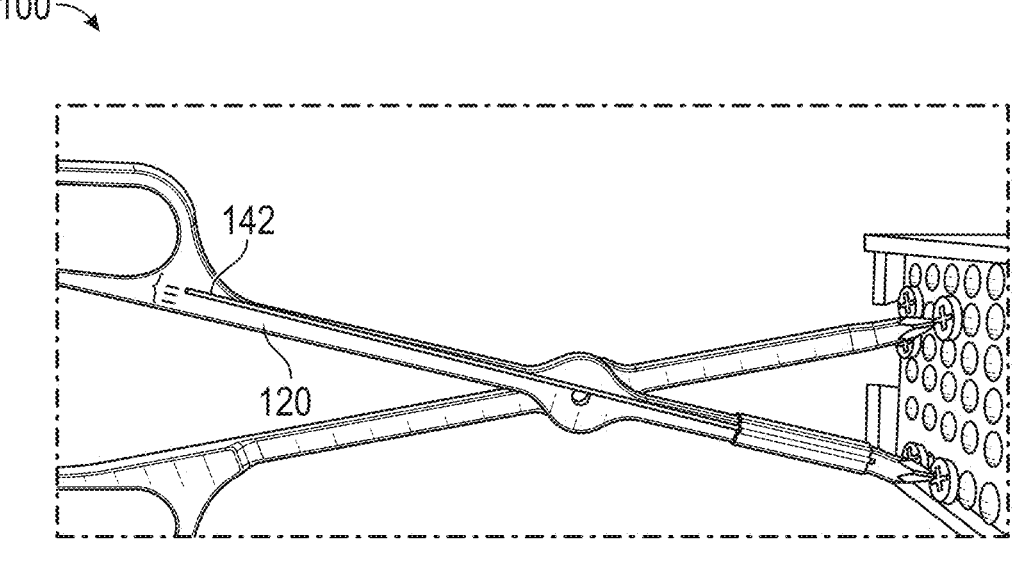
Figure 4A:
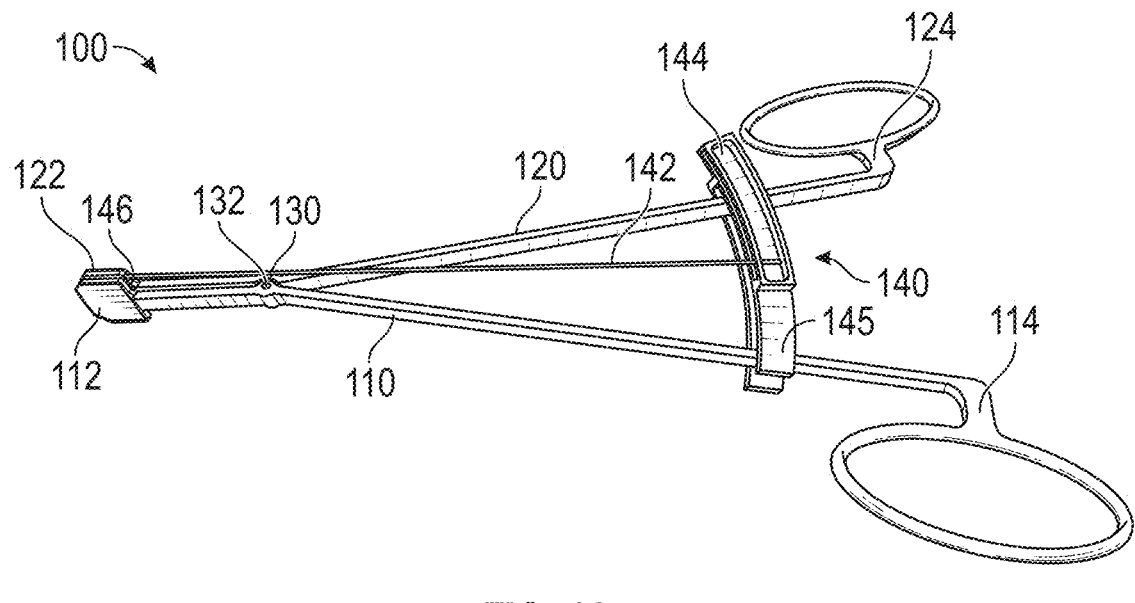
FIG. 4A shows a perspective view of the instrument for measuring and applying spinal compression force.
Figure 4B:
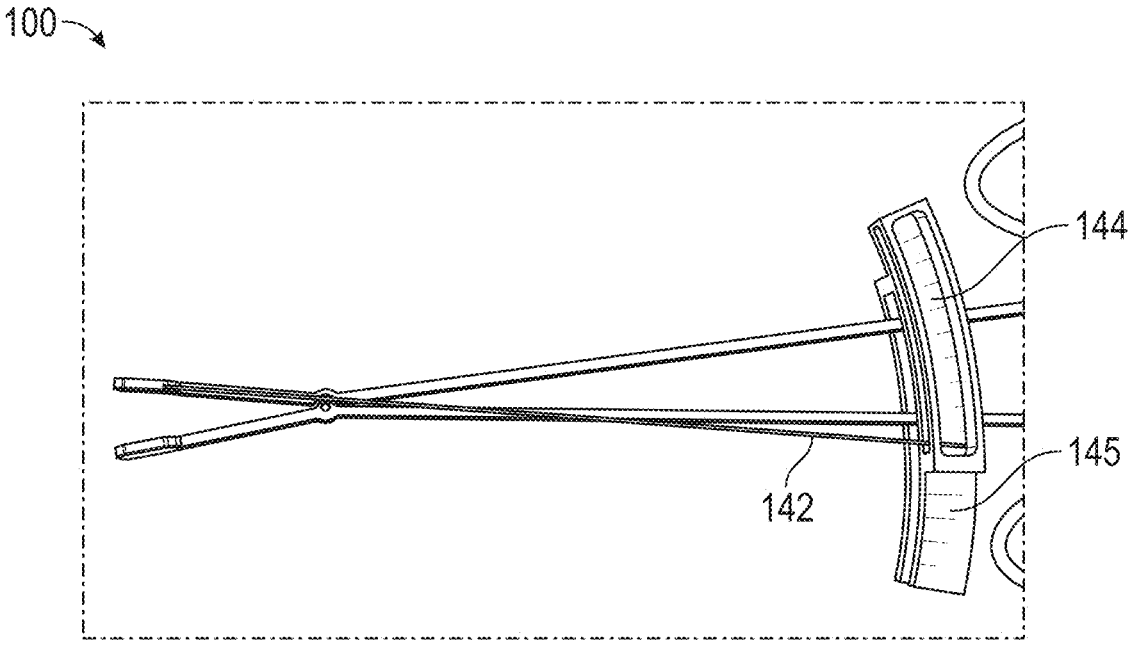
FIG. 4B shows a plan view of the instrument in another configuration, in accordance with some representative embodiments.

In some embodiments one or more of the arms includes one or more tips. As an example, in some embodiments, the first arm includes a first tip 112. In some embodiments, the second arm includes a second tip 122. Although the tips may include any feature of a tip used in connection with any tool or medical instrument, in some embodiments, at least one of the first tip 112 and the second tip 122 is configured to selectively couple to a spinal implant 500. For example, as shown in FIGS. 1-2B, in some embodiments, the tip 112, 122 is shaped and sized (e.g., comprises: a rounded end, a catch, a hook, a coupler, a projection, a screw head projection, a frictional engagement, a mechanical engagement, or any other suitable feature that is configured) to correspond to an anchor (e.g., a screw, nail, bolt, rivet, shaft, implant 500, or any other component configured to be attached to a patient's spine). In some embodiments, as shown in FIGS. 4A and 4B, the tip 112, 122 is configured to contact, couple directly to, or otherwise interface with the spine itself (e.g., by having a surface sized and shaped appropriately to contact a surface of a vertebra, being sized and shaped like a spinal implant, having a blade or planar portion, or otherwise being configured to interface with the spine).

Returning to FIGS. 1-4B, in some embodiments, one or more of the arms 110, 120 include one or more handles 114, 124. For example, in some cases, the first arm 110 includes a first handle 114. In some cases, the second arm 120 includes a second handle 124. Although one or both handles can include any feature useful for gripping the associated arm (either directly or through the intermediate use of a tool), such as one or more grips, protrusions, indentations, bars, slots, rings, or other gripping components, some embodiments of a handle include a ring. In some cases, the ring is configured to receive all or part of a thumb, hand, or one or more fingers of a user (e.g., a physician).

In accordance with the foregoing, some embodiments of the compressor 100 are configured such that applying a force to at least one of the first handle 114 and the second handle 124 causes at least one of the first tip 112 and the second tip 122 to apply the spinal compression force to the spine.

Some embodiments of the compressor 100 include one or more pivots 130. For example, in some cases, the first arm 110 and the second arm 120 are coupled together to form the pivot 130. Some embodiments include a pivot coupler 132 (e.g., a screw, bolt, nail, rod, thread, hinge, articulation, axis, joint, bearing, or any other type of fastener that could be used to couple multiple objects together to form a fulcrum, pivot, hinge, axle, spindle, or other static or dynamic connection point).

As shown in FIGS. 1-2B, in some embodiments, the first arm 110 is coupled to the second arm 120 (e.g., via the pivot 130) such that when the first arm is biased toward the second arm (e.g., when a user squeezes the handles 114, 124 toward each other), the first tip 112 is biased toward the second tip 122 (e.g., the tips come together, as with traditional scissors or pliers). In some such embodiments, squeezing the handles of the compressor 100 (or otherwise biasing one handle toward the other or both handles toward each other) causes the first and second tips, when coupled to spinal vertebrae, to place a compression force on one or more of the spinal vertebrae in question.

As shown in FIGS. 4A-4B, some embodiments of the compressor 100 include a configuration where the first arm 110 is coupled to the second arm 120 (e.g., via the pivot 130) such that when the first arm is biased toward the second arm, the first tip 112 is biased away from the second tip 122 (e.g., the tips diverge, as with reverse pliers). In some such embodiments, squeezing the handles of the compressor 100 (or otherwise biasing one handle toward the other or both handles toward each other) causes the first and second tips to separate from one another, thereby placing a compression force on one or more spinal vertebrae that may be located proximate to one of the tips.

In some embodiments, the first arm 110 and the second arm 120 are naturally biased towards or away from each other (e.g., via one or more spring disposed between or coupled to the arms, a tension rod, or any other suitable biasing mechanism) in order to maintain the compressor 100 in a closed or open configuration (as desired) when the compressor is at rest.

Although the compressor 100 can include any material useful for constructing a medical device, including one or more types of metal, metal alloy, ceramic, plastic, polymer, fiberglass, glass, or any other suitable material, some embodiments are formed of heat-resistant materials (e.g., metal) that can be placed into a sterilizing autoclave without being damaged or permanently deforming. Indeed, some embodiments lack one or more components that are not typically autoclave-safe (e.g., plastics, electronics, or other meltable or temperature-sensitive materials). In some embodiments, one or more components of the compressor (e.g., one or more arms 110, 120) are formed of flexible or resilient materials configured to deflect when the spinal compression force is applied (as discussed more fully below. The arms (and any other component of the compressor) may be any suitable length and thickness, and may include any suitable cross-sectional shape (e.g., circle, square, triangle, and any other regular or irregular shape) and any other desirable characteristic.

Figure 5A:
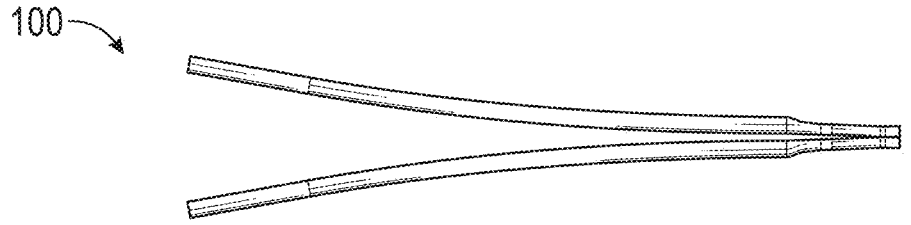
FIGS. 5A-5C show elevation views of various instruments that can be configured to measure and apply spinal compression force, in accordance with representative embodiments.
Figure 5B:
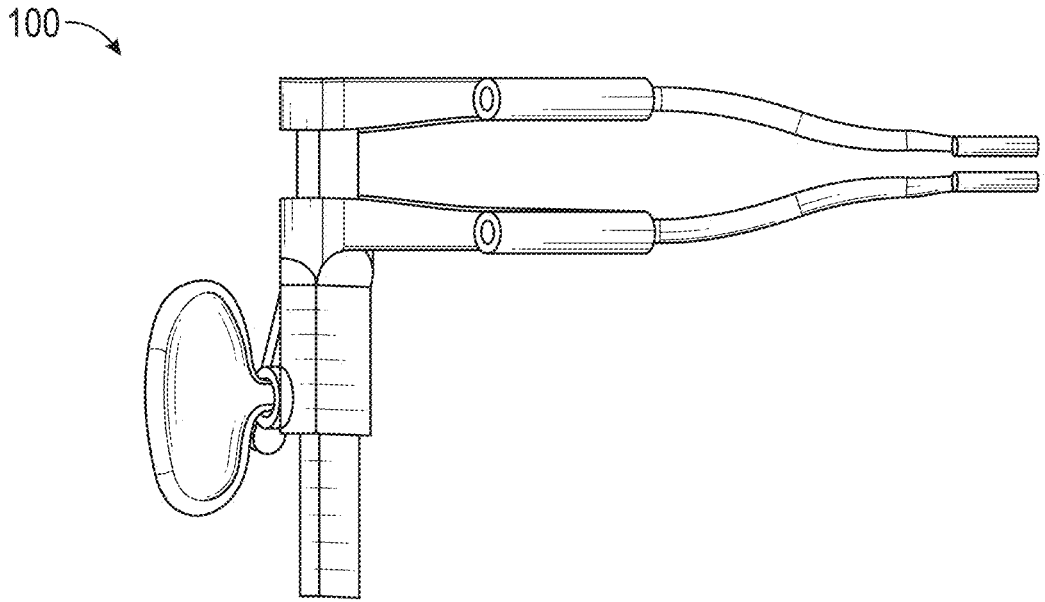
Figure 5C:
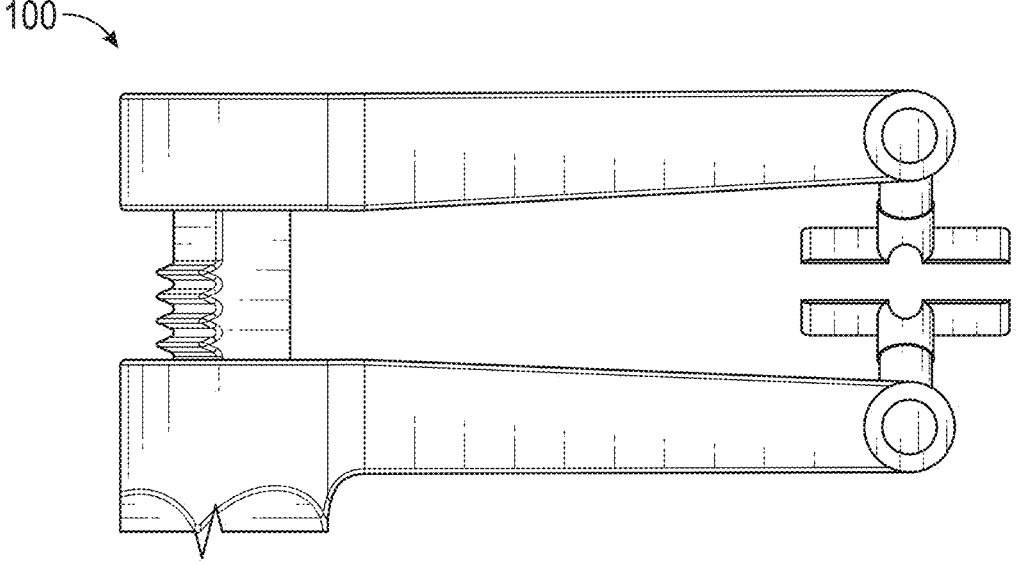

FIGS. 5A-C illustrate additional configurations for a compressor 100 that can be outfitted with additional components as discussed herein or otherwise adapted to form a compression instrument in accordance with this disclosure.

As shown in FIGS. 1-4B, some embodiments of the systems and methods include one or more gauges 140. While the gauge can include any component for measuring the compression force or conveying the value of the compression force to a user, some implementations of the gauge include one or more indicators 142. In some embodiments, the indicator is configured to convey a measurement of the spinal compression force to a user. While the indicator may include any component suitable for conveying such a measurement, some embodiments of the indicator include one or more needles, rods, shafts, bars, projections, arrows, sliders, dials, lasers, or other components configured to dynamically shift (e.g., change position, orientation, size, color, or any other perceivable characteristics) to display, emit, or otherwise convey one or more measurement values.

In some embodiments, the gauge 140 measures the compression force is based on the deflection of one or more flexible or resilient elements. In some embodiments, the flexible or resilient element includes an arm (e.g., one or more of the first arm 110, the second arm 120, or additional arms) that is configured to deflect (e.g., bend, bow, flatten, or otherwise flex) when the spinal compression force is applied. In this regard, some embodiments of the flexible or resilient element include a rod or another component with a known stiffness, such that the compression force can be determined based on the deflection distance.

In some embodiments, the indicator 142 is configured to measure the deflection of the flexible or resilient component. For example, in some cases, the indicator includes one or more needle (or rods, shafts, arrows, projections, bars, dials, lasers, or another components capable of indicating a measurement based on its position). The indicator, in some embodiments, is coupled to the flexible or resilient material. While the indicator may be coupled to the flexible or resilient material (e.g., an arm 110, 120) in any suitable manner, in some embodiments, the indicator is coupled to the flexible material only at (or only at) a single location, so that when the flexible or resilient material is deflected, the indicator remains in an undeflected configuration. In some embodiments, the indicator is coupled to the flexible or resilient material via one or more connectors 146. In some cases, the connector includes one or more sleeves, welds, rivets, joints, screws, nails, bolts, staples, frictional engagements, mechanical engagements, adhesives, ties, or other fasteners. Where the flexible material includes an arm 110, 120, in some embodiments, the indicator is coupled to the arm at or near the tip 112, 122 of the arm. In any case, some embodiments of the indicator are coupled to the flexible material within 1 mm, 2 mm, 3 mm, 5 mm, 10 mm, or 25 mm (or any subrange between 1 mm and 25 mm, or any other suitable distance) of the end that is configured to apply the compression force. Indeed, in some cases a more noticeable measurement may be obtained using a smaller indicator where the indicator is coupled as close to the force-applying end of the flexible material as possible.

In some embodiments, the gauge 140 includes one or more indicia 144. Although the indicia can include any suitable type of scales, markings, protrusions, grooves, notches, slots, colors, spectrums of color, or other indications of any kind that may aid a human in deciphering a measured value, in some cases, the indicia include one or more scales having markings that correspond to certain values of the compression force. For example, in some cases, when a specific amount of force (e.g., 5 newtons, 150 newtons, or any other specified amount of force) is applied to the arm 110, 120, the arm is deflected a certain distance, but the indicator 142 remains undeflected. Thus, in some cases, the distance between the initial position of the arm 110, 120 and its deflected position can be precisely determined through reference to the position of the indicator 142 relative to the arm. In some cases, the indicia 144 show a position of the arm relative to the needle. In some cases, the indicia include one or more markings for an initial position of the arm, a target position (or range) of the arm (for example, a position at which a desired compression force is applied by the arm), a warning position (e.g., where too much force is being applied), or any other useful position. Accordingly, in some embodiments, the indicia may greatly aid in making the determination of how much force is being applied, based on the deflection of the flexible or resilient component, as shown based on the relative position of the indicator (e.g., by including one or more markings to which the indicator points when the arm is deflected with 1, 5, 10, 20, 50, 100, 150, 200, 250, or 300 newtons of force, or any subrange thereof, or any other suitable amount of force). In some embodiments, the indicia include markings delineating an optimal compression force or an optimal range of compression force. In some cases, the indicia include markings in set force increments, and in some cases, the indicia include arbitrary markings based on desired measurements or historic results. While placement of the indicia on the instrument can be determined in any suitable manner (e.g., through calculation based on the known rigidity or any other suitable characteristic of one or more portions of instrument or in any other suitable manner), in some cases, a known amount of force is applied to one or more handles of the instrument and corresponding markings that align the needle with such known forces are placed on or are otherwise associated with the device.

Some embodiments include multiple sets of indicia. For example, as shown in FIGS. 4A and 4B, some embodiments include an alternative set of indicia 145 in addition to (or instead of) the indicia 144. These multiple sets of indicia may indicate different measurements. For example, in some embodiments, one set measures load (or compression force) and one set measures displacement.

To provide a specific illustrative example in accordance with some embodiments as described above, FIGS. 2A and 2B show a compression instrument having a compressor 100 and a gauge 140. In these illustrations, the compressor includes a first arm 110 coupled to a second arm 120 via a pivot coupler 132 of a pivot 130. Additionally, a first tip 112 and a second tip 122 are connected to an implant 500 (e.g., anchors configured to be attached to vertebrae of a patient). The gauge includes an indicator 142, in the case of these Figures being substantially in the shape of a needle. The indicator in these figures is coupled to the second arm 120 via a connector 146. Moreover, in these illustrations, the indicator points to indicia 144. In FIG. 2A, the indicator is pointing to a medial marking, as the instrument is at rest (e.g., no compression force, or very little compression force, is currently being applied). In FIG. 2B, a compression force is applied by squeezing a first handle 114 and a second handle 124, thereby biasing the first and second arms toward each other. As the arms are biased toward each other, the second arm 120 deflects slightly. Since the indicator 142 is only fixed to the second arm 120 near the tip 122, the indicator does not deflect along with the arm. Thus, the indicator in FIG. 2B now points to a position more lateral on the instrument than the resting position—as seen by the fact that the indicator now points to a more lateral marking.

Figure 3A:
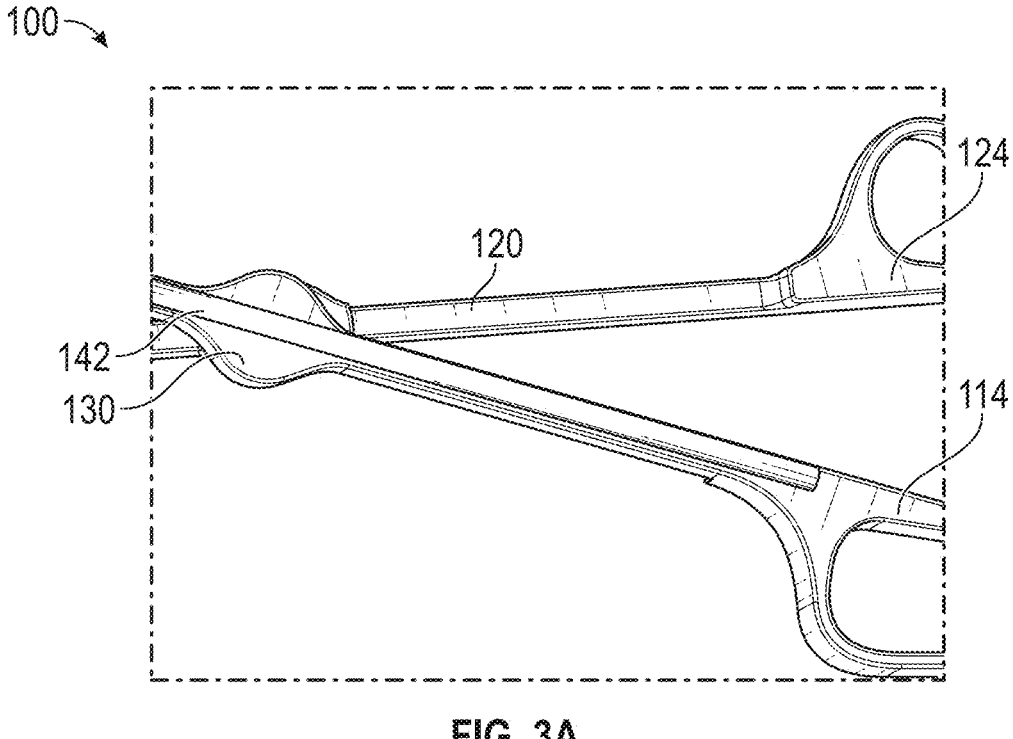
FIGS. 3A-3B show plan views of various configurations of the instrument for measuring and applying spinal compression force, in accordance with another representative embodiment.
Figure 3B:
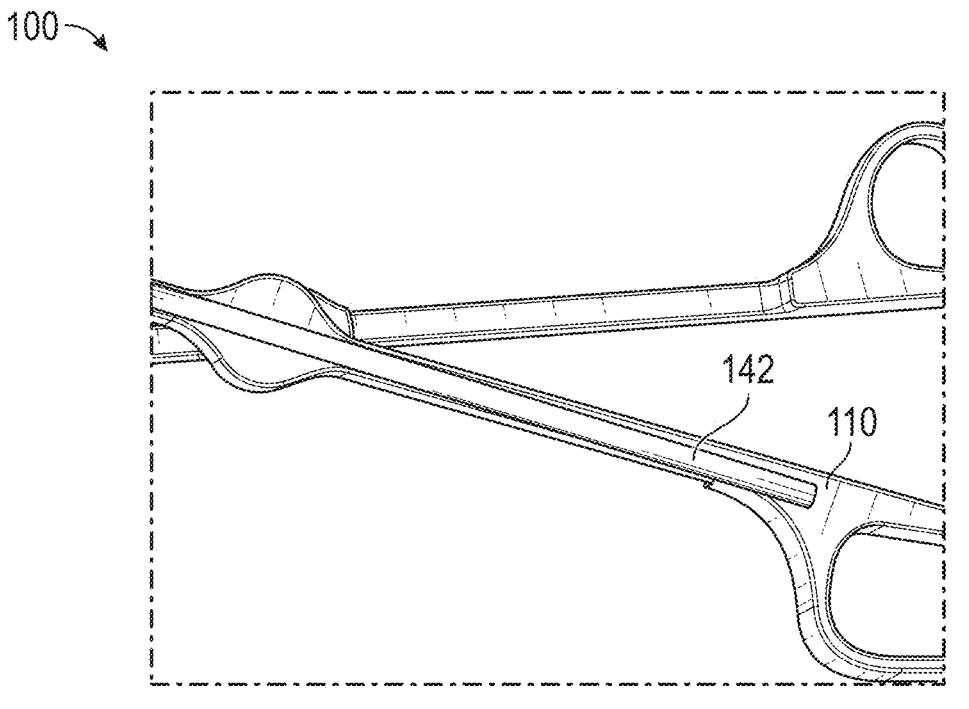

FIGS. 3A and 3B show a similar embodiment to FIGS. 2A and 2B. In this regard, FIG. 3A shows an indicator 142 that is flush with a first arm (110, as shown in FIG. 3B), while a compression force is not applied. When a compression force is applied, as shown in FIG. 3B (by squeezing handles 114, 124), the first arm 110 is deflected while the indicator remains straight, resulting in a noticeable offset between the indicator 142 and the first arm 110.

FIGS. 4A and 4B show another embodiment. In this embodiment, when a practitioner squeezes the handles 114, 124, the tips 112, 122 are biased away from each other as opposed to toward each other, due to the particular configuration of the pivot 130. Note that in both FIG. 4A and FIG. 4B, no compression force is applied, even though FIG. 4A shows the compressor 100 in a closed configuration, and FIG. 4B shows the compressor in an open configuration. As no force is applied, the indicator 142 points to the same location on the indicia 144 in both Figures (indicating that the load, or compression force, is zero). However, the position of the secondary indicia 145 is shifted with respect to the indicator 142, because the secondary indicia includes a displacement scale. In short, a wide variety of configurations for the gauge 140 are possible, including many indicators that provide measurements of force, displacement, or other characteristics based on the deflection, position, or other characteristics of one or more flexible or resilient elements.

Figure 6:
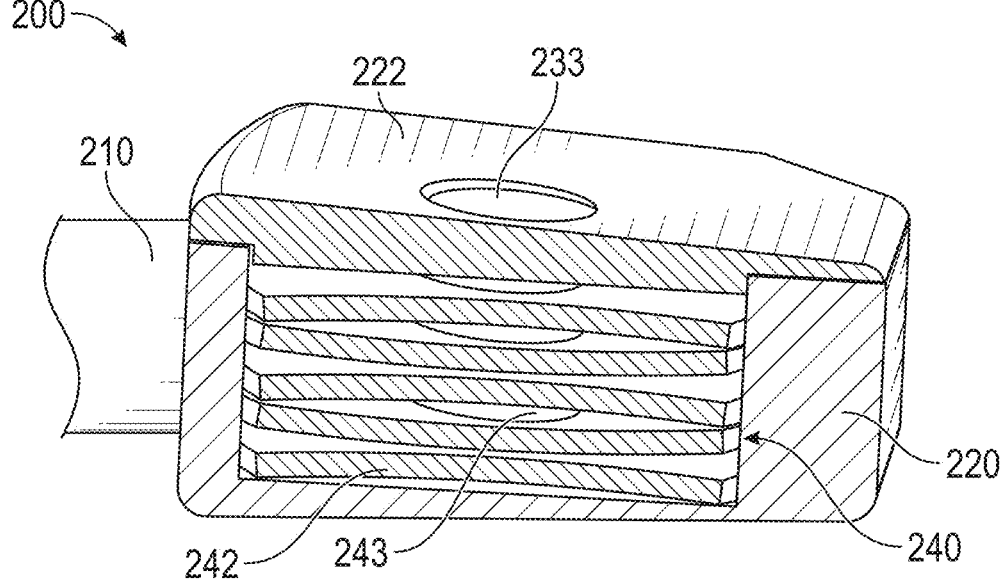
FIG. 6 shows a perspective view of the instrument for measuring and applying spinal compression force, in accordance with another representative embodiment.
Figure 7A:
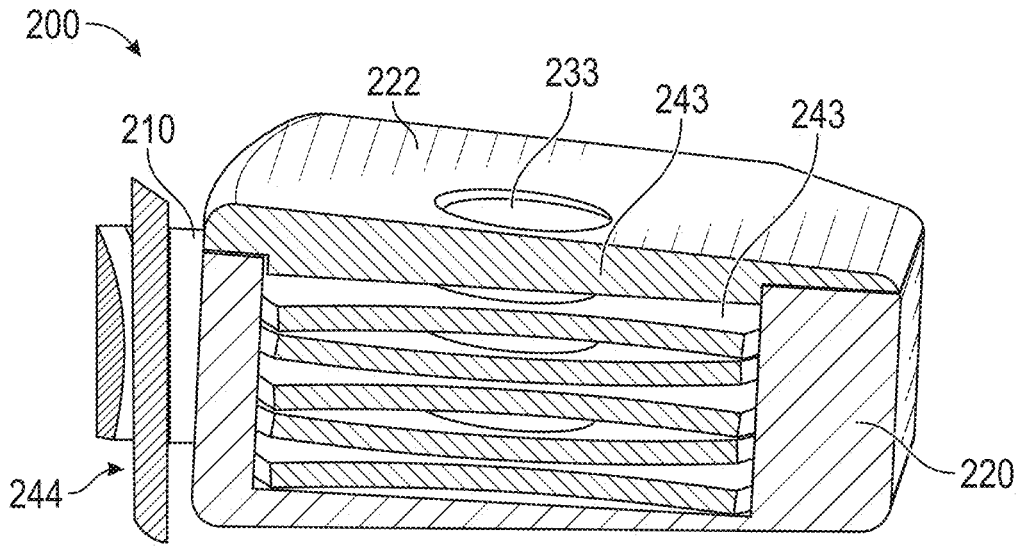
FIG. 7A shows a perspective view.
Figure 7B:
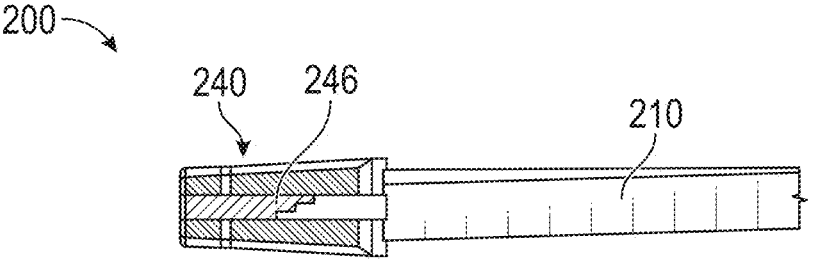
FIG. 7B shows an elevation view.
Figure 7C:
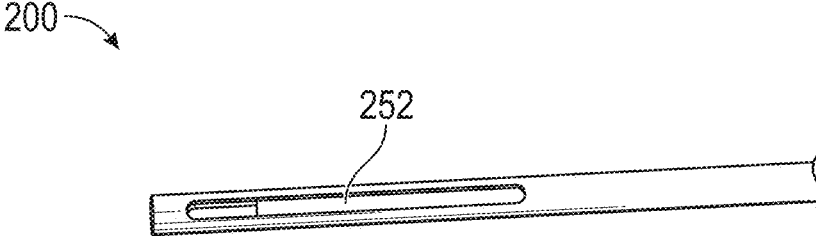
FIG. 7C shows a perspective view of a different embodiment of a portion of the instrument for measuring and applying spinal compression force, in accordance with some representative embodiments.

Turning now to FIGS. 6-7C, an alternative embodiment of a compression instrument is provided. Indeed, in some embodiments, the instrument includes a compressor 200 that is substantially in the form of a compression trial (instead of or in addition to a compressor that is substantially in the form of calipers).

In some embodiments, the compressor 200 optionally includes one or more housings 220. While the housing can include any component configured to form a particular shape or to house one or more other components, some embodiments of the housing are sized, shaped, and otherwise configured to be inserted into a spine. In some cases, the housing is configured to be inserted into a space between two vertebrae of the spine of the patient. Indeed, some iterations of the housing are configured to generally resemble a spinal implant trial. Some implementations include a trial arm 210, which, in some cases, is coupled to the housing. Although the housing can be formed of any material, some embodiments of the housing include a pliable or flexible material, thereby allowing for the housing to be freely compressed. Thus, in some iterations, compression discs 242 (or leaves) (as discussed in greater detail below) provide substantially greater resistance to compression than the housing.

Some embodiments include a gauge 240. As with other embodiments described herein, the gauge can include any component suitable for measuring a compression force or conveying the measurement to a user. That said, in some embodiments, the gauge includes one or more compression discs 242, which in some cases are disposed within the housing 220. Although some implementations have only a single compression disc, some embodiments include multiple compression discs. In some cases, the compression discs form a stack of discs.

In some embodiments, one or more compression discs 242 include one or more curved surfaces. In some cases, one or more of the curved surfaces are configured to flatten or become flatter when compressed. To illustrate, some implementations of the compression discs generally resemble a plate (or a disc, a ring, a sheet, or another substantially planar component) that is bent, bowed, flattened, or flexed, or that curves, ripples, undulates, or otherwise forms a shape that changes configuration when compressed. Thus, when the compression discs are compressed, the change in height of the compression discs (including a change in any particular compression disc on its own, or a change in a stack or collection of compression discs in the conglomerate) can be measured to determine a force. In some cases, the compression discs are pre-calibrated (e.g., the stiffness of the discs is known) to determine a precise force that correlates with a particular amount of change.

In some embodiments having multiple compression discs 242, a first compression disc and a second compression disc are situated (e.g., within the housing) so that the concave curved surface of the first compression disc faces a first direction and the concave curved surface of the second compression disc faces a second direction. For example, in some embodiments, the first disc faces with the concave curved surface pointed in a downward or posterior direction (e.g., away from a lid 222 of the housing 220) while the second disc faces with the concave curved surface pointed in an upward or anterior direction (e.g., toward the lid of the housing). In this manner, one or more gaps between the two discs (in a resting configuration) can be maximized so that a change in height of the stack, when compressed, is more pronounced. In some embodiments, multiple compression discs are directly adjacent to each other, or even in contact with one another, whereas in some instances, multiple compression discs are present within the housing but are separated from each other by a barrier or another component.

In some embodiments, the housing 220 includes one or more lids 222 or other openings. Indeed, in some cases, the housing includes a lid that is selectively removable. In some cases, the compression discs 242 are interchangeable, allowing for discs with different stiffnesses, curvatures, thicknesses, or other characteristics to be placed within the housing. In some instances, this configuration allows for different numbers of discs to be placed within the housing. Accordingly, in some cases, a single compressor 200 is useful for measuring multiple different ranges of compression forces.

As stated above, some embodiments of the compression instrument include a flexible or resilient element. In some cases, the flexible or resilient element includes a compression disc 242, configured to deflect when a spinal compression force is applied to the spine of the patient (e.g., in some cases a compression disc is configured to flatten or otherwise deform, deflect, or change to another configuration). In some embodiments, the gauge 240 is configured to measure the applied spinal compression force based on the deflection of the flexible or resilient element.

In some embodiments, the instrument includes indicia 244. For example, in some cases, the gauge includes an indicator. In some cases, a height of the housing serves as the indicator, or the housing itself functions as the indicator. In some cases, one or more characteristics of the compressor 200 compared with indicia 244 serves as the indicator of the gauge 240. Accordingly, in some cases, the gauge 240 is configured to measure a change in height or other dimension of the stack of compression discs 242.

In some embodiments, the gauge 240 includes one or more pressure gauges 250 (e.g., a device having a pressure indicator 252 for more accurately measuring a compression force). While such a pressure indicator can function in any suitable manner, in some embodiments, the compressor comprises an air tight chamber that is in fluid communication with the pressure sensor, such that when air pressure within the air tight chamber varies, so does the reading on the pressure indicator. Moreover, some embodiments include one or more integrated scales 246, hydraulic or pneumatic lifts configured to apply a known pressure, or other components for measuring a spinal compression force applied to a patient's spine.

In some embodiments, when a desired spinal compression force is applied using the compressor 200 (as determined by the gauge 240), a spinal implant of the proper size (e.g., the size that would apply the desired amount of compression force) is inserted into the space between two vertebrae of spine where the compression force was measured.

Referring now to all of FIGS. 1-7C, some embodiments of the systems and methods disclosed herein include a method for applying and measuring a spinal compression force. In some cases, the method includes one or more of the following: obtaining one or more compression instruments for applying one or more spinal compression forces (e.g., instruments including one or more compressors 100, 200); obtaining one or more gauges 140, 240 for measuring the spinal compression force; applying the spinal compression force with the instrument; and measuring the spinal compression force with the gauge.

In some embodiments, the application of the spinal compression force with the instrument includes gradually increasing an application of the spinal compression force until the spinal compression force reaches a desired value, as measured with the gauge 140, 240. In some embodiments, the desired value is anywhere between 1 newton and 000 newtons (or any subrange thereof). For example, in some implementations, the desired value is approximately between 50 and 250 newtons, and, in some implementations, the desired value is between approximately 75 newtons and approximately 150 newtons.

In some embodiments, the method includes measuring a distance between two spinal vertebrae when the spinal compression force reaches the desired value. In some cases, the measuring a distance is done with a tool separate from the one used to apply the compression, but in some cases the same tool is used for applying the compression and measuring the distance (and, in some cases, measuring the compression force as well). In some cases, the method includes inserting an implant having a thickness approximately equal to the measured distance.

In some embodiments, the applying the spinal compression force includes inducing a deflection in a flexible material. In some embodiments, the measuring the compression force includes measuring the deflection in the flexible or resilient material and calculating the force based on the characteristics (e.g., the stiffness and other characteristics) of the flexible material. In some embodiments, the method includes calibrating the instrument through application of a known force to determine the characteristics of the flexible material. In some embodiments, the method includes adjusting the stiffness of the flexible material. In some cases, the adjusting the stiffness includes varying a length of the flexible material, a cross-sectional area of the flexible material, or the material itself.

The systems and methods described herein may be modified in any suitable manner. Some embodiments of the disclosed systems and methods include a system for applying a desired amount of compression force to a patient's spine. In some instances, the system includes an instrument configured to apply a trial force to a pair of vertebrae of the patient's spine. While the instrument may be any suitable instrument (as discussed herein), in some embodiments, the instrument includes one or more of a flexible or resilient element (e.g., an arm 110, 120, a compression disc 242, or another flexible or resilient component) configured to deflect upon application of the trial force. In some embodiments, the instrument includes a gauge 140, 240 for measuring the trial force based on a degree of deflection of the flexible or resilient element. In some implementations, the system includes a spinal implant 500 configured to apply the desired amount of compression force to the patient's spine, in accordance with the trial force as measured. In some cases, the system includes a plurality of spinal implants having differing characteristics (e.g., different thicknesses, different materials, different stiffnesses, etc.), thereby allowing a physician to select a suitable spinal implant having the desired characteristics based on an applied compression force determined to be suitable through measurement of the force.

Some embodiments include one or more tools for measuring displacement. As an example, some embodiments include a tool for measuring the displacement of one or more spinal vertebrae. In some embodiments, the tool for measuring displacement shows a measurement of the displacement of spinal vertebrae at the point when the desired amount of spinal compression force is applied (e.g., when a gauge 140, 240 indicates that a desired value of force is being applied). Although the tool for measuring displacement can include any component suitable for measuring displacement, some embodiments include one or more gauges, indicators, indicia, alternative indicia, markings, rulers, scales, or any other components that may be useful for measuring displacement (such as any of the components discussed herein).

In some embodiments, the tool for measuring displacement is separate from a compression instrument (e.g., provided separately from a compressor 100, 200, or a gauge 140, 240), but in some embodiments, the tool for measuring displacement is integrated with the compression instrument. As an example, FIGS. 4A-4B show a tool that includes alternative indicia 145 for measuring displacement. In FIG. 4A, the tips 112, 122 of the compressor 100 are in a closed position, so the alternative indicia 145 do not show any displacement. In FIG. 4B, however, the tips are in an open position, and the tool for measuring displacement shows a corresponding shift in the indicia. Accordingly, in some embodiments once a desired compression force is obtained, the displacement can be measured, and an implant having a size that approximately corresponds to the measured displacement can be selected.

The various embodiments disclosed herein may be used separately or in combination with each other. As an example, in some embodiments a compression trial (e.g., the compressor 200 of FIG. 6) is used in connection with a set of compression calipers (e.g., the compressor 100 of FIG. 1). For instance, one or more tips (e.g., the first and second tips 112, 122 of FIG. 1) of a compressor may include a compression gauge (e.g., the gauge 240 of FIG. 6) including one or more compression discs (e.g., 242 of FIG. 6), instead of or in addition to a deflection gauge (e.g., the gauge 140 of FIG. 1).

Additionally, it should be noted that in some cases, the flexible or resilient member or element (as in is flexible but not resilient, such that when the member or element is deformed, it maintains its shape to allow for a compression force to be easily measured, even after the compression instrument has been removed from the patient. In some cases, however, the flexible or resilient member or element is both flexible and resilient such that the compression instrument returns to its original shape between uses and can be reused one or more times (e.g., many times following autoclaving).

As the systems and methods disclosed herein are compatible with one another, the systems discussed herein can be used in practicing the methods disclosed herein, and vice versa. Accordingly, the method may further include implementing, exercising, or otherwise using any of the components discussed herein for any of their stated or intended purposes, as reasonably predictable and understood by a person of ordinary skill in the art. The systems disclosed herein can be made in any suitable manner, and they may be used in any way consistent with their operational capabilities. Moreover, in some cases, any particular element or elements of any apparatus—or portion or portions of any method—disclosed herein can be omitted.

As used herein, the singular forms "a", "an", "the" and other singular references include plural referents, and plural references include the singular, unless the context clearly dictates otherwise. For example, reference to an indicator includes reference to one or more indicators, and reference to compression discs includes reference to one or more compression discs. In addition, where reference is made to a list of elements (e.g., elements a, b, and c), such reference is intended to include any one of the listed elements by itself, any combination of less than all of the listed elements, and/or a combination of all of the listed elements. Moreover, the term "or" by itself is not exclusive (and therefore may be interpreted to mean "and/or") unless the context clearly dictates otherwise. Furthermore, the terms "including", "having", "such as", "for example", "e.g.", and any similar terms are not intended to limit the disclosure, and may be interpreted as being followed by the words "without limitation".

In addition, as the terms "on", "disposed on", "attached to", "connected to", "coupled to", etc. are used herein, one object (e.g., a material, element, structure, member, etc.) can be on, disposed on, attached to, connected to, or otherwise coupled to another object—regardless of whether the one object is directly on, attached, connected, or coupled to the other object, or whether there are one or more intervening objects between the one object and the other object. Also, directions (e.g., "front", "back", "on top of", "below", "above", "top", "bottom", "side", "up", "down", "under", "over", "upper", "lower", "lateral", "right-side", "left-side", "base", etc.), if provided, are relative and provided solely by way of example and for ease of illustration and discussion and not by way of limitation.

The described systems and methods may be embodied in other specific forms without departing from their spirit or essential characteristics. The described embodiments, examples, and illustrations are to be considered in all respects only as illustrative and not restrictive. The scope of the described systems and methods is, therefore, indicated by the appended claims rather than by the foregoing description. All changes that come within the meaning and range of equivalency of the claims are to be embraced within their scope. Moreover, any component and characteristic from any embodiments, cases, iterations, implementations, examples, Figures, and illustrations set forth herein can be combined in any suitable manner with any other components or characteristics from one or more other embodiments, cases, iterations, implementations, examples, Figures, and illustrations described herein.

What is claimed is:

1. An instrument for applying and measuring a spinal manipulation force, the instrument comprising:
    a manipulator configured to apply the spinal manipulation force to a spine of a patient, the manipulator comprising:
        a first arm having a first tip and a first handle; and
        a second arm having a second tip and a second handle; and
    a gauge for measuring the spinal manipulation force, the gauge comprising
    an indicator,
    wherein:
        applying a force to at least one of the first handle and the second handle when the manipulator is coupled to the spine causes at least one of the first tip and the second tip to apply the spinal manipulation force to the spine;
        the first arm comprises a resilient material configured to deflect when the spinal manipulation force is applied to the spine; and
        a portion of the first arm is configured to change position with respect to a portion of the gauge to indicate an amount of deflection of the resilient material when the spinal manipulation force is applied to the spine.

2. The instrument of claim 1, wherein at least one of the first tip and second tip is configured to selectively contact surface of a vertebra.

3. The instrument of claim 1, wherein at least one of the first tip and the second tip is configured to selectively couple to a spinal implant.

4. The instrument of claim 1, wherein the first arm and the second arm are coupled together to form a pivot.

5. The instrument of claim 4, wherein the pivot couples the first arm to the second arm such that when the first arm is biased toward the second arm, the first tip is biased toward the second tip.

6. The instrument of claim 4, wherein the pivot couples the first arm to the second arm such that when the first arm is biased toward the second arm, the first tip is biased away from the second tip.

7. The instrument of claim 1, wherein the indicator is configured to convey a measurement of the spinal manipulation force to a user.

8. The instrument of claim 1, wherein the instrument further comprises a tool for measuring displacement of one or more vertebrae.

9. A method for applying and measuring a spinal manipulation force, the method comprising:
    obtaining an instrument for applying a spinal manipulation force, the instrument comprising:
        a manipulator configured to ply the manipulation force to a spine of a patient, the manipulator comprising:
            a first arm having a first tip and a first handle, the first arm comprising a resilient material configured to deflect when the spinal manipulation force is applied to the spine; and a second arm having a second tip and a second handle; and a gauge for measuring the spinal manipulation force the gauge comprising a indicator;

applying the spinal manipulation force with the instrument, thereby causing a portion of the first arm to change position with respect to a portion of the gauge to indicate an amount of deflection of the resilient material when the spinal manipulation force is applied to the spine; and measuring the amount of deflection with the gauge.

10. The method of claim 9, wherein the applying the spinal manipulation force with the instrument comprises gradually increasing an application of the spinal manipulation force until the spinal manipulation force reaches a desired value, as measured with the gauge based on the amount of deflection of the resilient material.

11. The method of claim 10, wherein the desired value is between approximately 75 newtons and approximately 125 newtons.

12. The method of claim 10, further comprising measuring a distance between two spinal vertebrae when the spinal manipulation force reaches the desired value, and inserting an implant having a thickness approximately equal to the distance as measured.

13. An instrument for applying and measuring a spinal manipulation force, the instrument comprising:

a manipulator configured to apply the spinal manipulation force to a spine of a patient, the manipulator comprising:

a first arm having a first tip and a first handle; and a second arm having a second tip and a second handle; and a gauge for measuring the spinal manipulation force, the gauge comprising:

an indicator; and indicia configured to show a position of the first arm with respect to the indicator, wherein when the first tip and the second tip are coupled to the spine and the spinal manipulation force is applied, the first arm is configured to resiliently deflect, thereby changing the position of the first arm with respect to the indicator.

14. The instrument of claim 13, wherein at least a portion of the gauge is disposed between the first handle and the second handle.

15. The instrument of claim 13, wherein the instrument is autoclave-safe.

16. The instrument of claim 13, wherein at least one of the first tip and the second tip is configured to selectively contact a surface of a vertebra.

17. The instrument of claim 13, wherein the first arm is coupled to the second arm at a pivot.

18. The instrument of claim 17, wherein the pivot couples the first arm to the second arm such that when the first arm is biased toward the second arm, the first tip is biased away from the second tip.

19. The instrument of claim 17, wherein the indicator comprises an elongated component having a first end and a second end, wherein the first end of the elongated component is coupled to at least one of (i) the first arm near the first tip and (ii) the second arm near the second tip.

* * * * *